United States Patent
Spalka

(10) Patent No.: US 8,195,951 B2
(45) Date of Patent: Jun. 5, 2012

(54) DATA PROCESSING SYSTEM FOR PROVIDING AUTHORIZATION KEYS

(75) Inventor: Adrian Spalka, Koblenz (DE)

(73) Assignee: CompuGroup Medical AG, Koblenz (DE)

( * ) Notice: Subject to any disclaimer, the term of this patent is extended or adjusted under 35 U.S.C. 154(b) by 0 days.

(21) Appl. No.: 13/123,292

(22) PCT Filed: Sep. 18, 2009

(86) PCT No.: PCT/EP2009/062093
§ 371 (c)(1),
(2), (4) Date: Jun. 13, 2011

(87) PCT Pub. No.: WO2010/040629
PCT Pub. Date: Apr. 15, 2010

(65) Prior Publication Data
US 2012/0036368 A1 Feb. 9, 2012

(30) Foreign Application Priority Data

Oct. 10, 2008 (DE) ...................... 20 2008 013 415 U

(51) Int. Cl.
*H04L 29/06* (2006.01)
(52) U.S. Cl. ........................................ 713/182; 380/281
(58) Field of Classification Search .................. 713/182; 380/281
See application file for complete search history.

(56) References Cited

U.S. PATENT DOCUMENTS

| | | | |
|---|---|---|---|
| 7,552,333 B2 * | 6/2009 | Wheeler et al. ............... | 713/176 |
| 7,860,797 B2 | 12/2010 | Michelsen | |
| 2004/0172538 A1 | 9/2004 | Satoh | |
| 2008/0301463 A1 | 12/2008 | Michelsen | |

FOREIGN PATENT DOCUMENTS

| | | |
|---|---|---|
| DE | 10258769 A1 | 6/2004 |
| DE | 102004051296 B3 | 5/2006 |

(Continued)

OTHER PUBLICATIONS

RSA Laboratories, "What is Public Key Cryptography?", http://www.rsa.com/rsalabs/node.asp?id=2165, pp. 1-2, Mar. 3, 2007 from Internet Archive WayBack Machine.*

(Continued)

*Primary Examiner* — Nasser Goodarzi
*Assistant Examiner* — Lisa Lewis
(74) *Attorney, Agent, or Firm* — Matthew B. Dernier, Esq.; Gibson & Dernier LLP

(57) ABSTRACT

A computer-implemented method for providing authorization keys, where the method includes receiving a further asymmetrical, cryptographic key pair, where the further asymmetrical key pair is part of a key pair sequence, where the further asymmetrical key pair includes a further first and a further second authorization key; retrieving a ciphertext, where the ciphertext is associated with the key pair which immediately precedes the further key pair in the sequence of key pairs, where the ciphertext includes the initial first key encrypted with the second authorization key of the key pair which immediately precedes the further key pair in the sequence of key pairs; decrypting the initial first authorization key using the first authorization key of the key pair which immediately precedes the further key pair in the sequence of key pairs; generating a further ciphertext through encryption of the decrypted initial first authorization key using the second authorization key of the further key pair; and saving the further ciphertext.

26 Claims, 8 Drawing Sheets

FOREIGN PATENT DOCUMENTS

WO 2006029820 A1 3/2006

OTHER PUBLICATIONS

International Search Report for corresponding application PCT/EP2009/062093, Feb. 11, 2011.
Schneier B Ed. "Applied Cryptography, Passage" Jan. 1, 1996, Applied Cryptography Protocols, Algorithms, and Source Code in C. John Wiley & Sons, Inc., New York, pp. 173-175 (XP-000864254).
Owens L., et al., :An Identity Based Encryption System, Proceedings of the 3rd International Symposium on Principles and Practice of Programming in Java (PPPJ "04)., Las Vegas, Nevada, Jun. 16, 2004, pp. 154-159.
Schneier B. "Applied Cryptography" Jan. 1, 1996, John Wiley & Sons, Inc., New York, pp. 52-53 (XP-002619016).
International Preliminary Report on Patentability for corresponding PCT Application No. PCT/EP2009/062093, Apr. 8, 2011.

* cited by examiner

DATA PROCESSING SYSTEM FOR PROVIDING AUTHORIZATION KEYS

BACKGROUND

The invention relates to a computer program product comprising processor-executable instructions for carrying out method steps for providing authorization keys, a computer program product for carrying out method steps for decrypting a data object, and a data processing system.

The electronic health card, abbreviated in German to eGK, is intended in future to replace the health insurance card in Germany. The aim here is to reduce the cost of, simplify and expedite data communication between medical service providers, medical insurance companies, pharmacies and patients in future. This also includes, inter alia, allowing access to an electronic doctor's letter, an electronic medical record and an electronic prescription with the aid of the electronic health card.

By way of example, medical data objects (MDOs) such as an electronic doctor's letter, an electronic medical record or an electronic prescription can thus be encrypted and stored in a digitally signed fashion on a central server. In this case, encryption is preferably effected by means of a symmetrical key which is individually randomly generated for each new medical data object of an electronic medical record such as e.g. an electronic doctor's letter or an electronic prescription. The symmetrical key itself, after it has been created, is for example encrypted with a public key and stored together with the encrypted medical data objects on the central server. In this case, said public key used for encryption forms, together with a private key stored on the electronic health card, a cryptographic asymmetrical key pair. This ensures that access to the encrypted medical data objects is possible exclusively using the secret health card key. In the event of such access, firstly the encrypted symmetrical key is decrypted by means of the secret health card key, whereupon further decryption of the medical data objects is then possible with the decrypted symmetrical key. If, during the creation of an MDO, a digital signature was also generated with the secret health card key, then the integrity of the MDO and the authenticity of the MDO generator can subsequently be verified by means of the digital signature.

By way of example, DE 10 2004 051 296 B3 discloses a method for storing data and for interrogating data, and corresponding computer program products. A personalized smart card allows storage of a virtual patient file on a data server. Using the smart card, data, such as an MDO of a patient file, for example, can be encrypted by an office EDP system of a doctor's office and be transmitted in digitally signed fashion to a data server.

DE 102 58 769 A1 discloses a further application of smart cards for patient data.

When the electronic health card is used, the problem arises that, in the case of, for example, a change of medical insurance company and the associated issuing of a new electronic health card with corresponding new asymmetrical key pairs, it is no longer possible to access without problems an electronic medical record previously encrypted using the old electronic health card.

SUMMARY OF THE INVENTION

Against this background, the invention is based on the object of providing an improved computer program product for carrying out method steps for providing authorization keys, an improved computer program product for carrying out method steps for decrypting a data object, and an improved data processing system.

The objects on which the invention is based are respectively achieved by means of the features of one or more embodiments disclosed and/or described herein.

According to the invention, the invention relates to a computer program product comprising processor-executable instructions for carrying out method steps for providing authorization keys, wherein the method comprises the step of receiving a further asymmetrical cryptographic key pair, wherein the further asymmetrical key pair is part of a key pair sequence, wherein the further asymmetrical key pair comprises a further first and a further second authorization key. This is followed by retrieving a ciphertext, wherein the ciphertext is assigned to the key pair which immediately precedes the further key pair in the sequence of key pairs, wherein the ciphertext comprises the initial first key encrypted with the second authorization key of the key pair which immediately precedes the further key pair in the sequence of key pair. This is followed by decrypting the initial first authorization key with the first authorization key of the key pair which immediately precedes the further key pair in the sequence of key pairs. This is followed by generating a further ciphertext by encrypting the decrypted initial first authorization key with the second authorization key of the further key pair. This is followed, finally, by storing the further ciphertext.

Carrying out the method steps mentioned has the advantage that, with any desired asymmetrical cryptographic key pairs within a sequence of key pairs, it is ensured that data objects that were encrypted using one of the asymmetrical cryptographic key pairs of the sequence of key pairs can be decrypted again. For decryption, the "original" key pair used for the original encryption is not necessary for this purpose.

Preferably, the procedure is such that new data objects are encrypted, in principle, with the initial second authorization key. Using any desired key pair of the sequence of asymmetrical cryptographic key pairs, it is thereupon possible, by correspondingly accessing the ciphertext assigned to the respective key pair, to provide the initial first authorization key, with which, in turn, decryption of the data object is possible.

In order to carry out the method steps mentioned, in order to use a new or further asymmetrical cryptographic key pair for processes of encryption and decryption of data objects, the only prerequisite, therefore, is that a corresponding user is in possession of the asymmetrical cryptographic key pair which immediately precedes the new key pair in the sequence of key pairs. In one practical example of health cards, this would thus mean that an owner of a new electronic health card, for the "activation" thereof, takes just once the previously used old electronic health card to a corresponding health service provider or generally a trustworthy center. Using the old and the new electronic health cards, the new ciphertext is thereupon generated, by means of which it is possible to securely access encrypted data objects with the old and with the new electronic health card.

According to one embodiment of the invention, the ciphertext is stored in a database. By way of example, a database of a central trustworthy center can be used here.

According to a further embodiment of the invention, the computer program product furthermore comprises instructions for carrying out the step of generating the further asymmetrical cryptographic key pair, wherein the instructions comprise the following steps:

1. Receiving a unique user identification id and a user identifier pw that can be chosen as desired and is assigned to the user identification;
2. Mapping the user identifier onto a value by means of a function g. The function g can be the identity function or a non-trivial function. From the standpoint of security and confidentiality, g is preferably chosen as a collision-free one-way function, such as e.g. a cryptographic hash function;
3. Generating a random value z;
4. Calculating the further first data object key by applying a function f to g (user identifier) and z. By way of example, g (user identifier), i.e. the result of applying the function g to the user identifier, and z are concatenated with one another and the function f is applied to the result of this concatenation. By way of example, f can be a cryptographic hash function that is applied to the concatenation of the hash value of the user identifier and the random value z;
5. Calculating the further second data object key from the further first data object key, wherein the further first and the further second data object keys form an asymmetrical cryptographic key pair. By way of example:
    for elliptical curves, the further second data object key, which is a point on the elliptical curve, can be calculated by multiplying the first data object key, which constitutes an integer, by the base point from the domain parameters;
    for RSA, the further second data object key (an integer) is calculated in such a way that with the first data object key (likewise an integer) it meets a congruence relation defined in the RSA method.

Carrying out the method steps mentioned has the advantage that asymmetrical cryptographic key pairs can be generated here, wherein this is effected using a user identifier that can be chosen as desired. The user identifier itself is included in the calculation algorithm for the further first and further second data object keys.

In the case where the computer program product according to the invention is used in the context of the electronic health card, a user is able to access their patient data either using their electronic health card, or else using the user identifier chosen by said user. If a user decides, additionally alongside their electronic health card, also to enable the possibility of password-based access to their patient data, then in this case, too, preferably by a trustworthy center once after the user identifier has been input, the corresponding further asymmetrical cryptographic key pair is generated and the ciphertext is created using the electronic health card that is additionally in the patient's possession, such that data objects previously enciphered using the electronic health card can also be accessed by means of the user identifier chosen further, wherein this also holds true in the opposite order.

This method for generating an asymmetrical cryptographic key pair thus differs from conventional key generating methods, in which, according to current prior art, only an assignment of a user identifier that can be chosen as desired to an associated generated cryptographic key pair is possible, but not a functional calculation of key pairs using the actual user identifier that can be chosen as desired, in which the permanent storage of the assignment of the user identifier to the key is omitted.

In previously customary methods, a user identifier chosen as desired or the mapping thereof is stored in a table and uniquely assigned to public and private keys, wherein it is stipulated only by administrative and/or legal regulations that unauthorized persons are not permitted to have access to the private key. This procedure considerably impairs security: if an unauthorized person or else a state agency, on account of diverse surveillance laws, acquires access to the database which assigns the passwords to the public and private keys, then this person or organization is immediately able to acquire access to all the data objects of a person by access to this individual key-managing institution.

The method for generating an asymmetrical cryptographic key pair thus has the advantage that, together with the possibility of a user identifier that can be chosen as desired, no central entity can obtain possession of the combination of user identifier (e.g. password) and key pairs. The further first data object key can only be calculated with knowledge of a random value and the user identifier. The generation of the further second data object key likewise requires knowledge of the random value and the user identifier, wherein the user identifier is preferably exclusively secretly known to the corresponding user. It is thus no longer possible, for example, by impoundment of or theft from central database servers, to acquire access to data object keys and thus to encrypted data without active assistance of those persons who are in possession of their private, secret user identifiers.

A further advantage of the method according to the invention is that even when the same user identifier is chosen by different users, on account of the inclusion of the random value when generating the further first data object key, it can be ensured that the same key pair is never assigned to different users.

It should be pointed out here that embodiments of the method according to the invention for generating an asymmetrical cryptographic key pair can be applied to any desired cryptosystems for generating asymmetrical key pairs, such as, for example, the RSA cryptosystem, the Rabin cryptosystem, and the Elgamal cryptosystem, or cryptographic methods on elliptical curves. The further second data object key is calculated from the further first data object key obtained on the basis of the user identifier and the random value, wherein such methods can be applied for this calculation.

For this purpose, it may be necessary that the further first data object key has to have one or more predefined properties and/or has to meet conditions which are checked in the context of a permissibility check. If the further first key proves to be impermissible for a chosen method, then a new random value is generated in order to generate a new candidate for a further first data object key, which is then in turn subjected to a permissibility check. This is repeated until a permissible further first data object key has been found. Said permissibility check can include restrictions which arise directly from the algorithm for carrying out a corresponding asymmetrical cryptographic key generating method.

Moreover, further limitations can also be included in the permissibility check, said further limitations e.g. relating to the entropy of the generated key or arising from present insights with regard to the attackability of the corresponding key generating method. By way of example, for the RSA method there are a series of generally known and regularly supplemented restrictions, compliance with which during key generation is required by authorities in order to minimize the attackability of the generated key pairs. By way of example, PKCS#1 (public key cryptography standards) specifies a series of cryptographic specifications for RSA which have to be complied with by public and private RSA key pairs. The standard PKCS#13, which is in the development stage, will establish the requirements made of key generation on elliptical curves.

One aspect of the invention is that the calculation of the further first data object key is effected using a function g, applied to the user identifier pw. According to one embodiment, either the user identifier that can be chosen as desired is received as such and thereupon converted using the function g, or the function value g(pw) is received directly.

The calculation of the further first data object key using the value b=g(pw) and the random value z has the advantage that, from comparatively insecure user identifiers, it is thus possible to calculate input values which have a high randomness and therefore further increase the security of the first data object key in an effective manner during the calculation of said first data object key. By way of example the cryptographic hash function SHA-256 is applied for g.

According to a further embodiment of the invention, the further first data object key is calculated by applying a function f to the values b and z. By way of example, f can be defined as the application of the cryptographic hash function SHA-256 to the concatenation, that is to say linking together, of b and z.

Applying the function f to the random value z and the function value g(pw) ensures a high quality of the further first data object key. In other words, on account of the random choice of z, the further first data object key likewise has a high randomness, thereby making it practically impossible to guess the further first data object key.

According to one embodiment of the invention, the key pair is calculated for a cryptosystem on elliptical curves. An elliptical curve is given by the equation $y^2=x^3+ax+b$, where the parameters a and b and also the coordinates of the points (x, y) on the curve are integers from the interval $[0, n-1]$. The values a, b, n, and a chosen curve point P, form the so-called domain parameters of the elliptical curve, which have to be concomitantly disclosed in order to carry out cryptographic methods using the further first and further second keys. The number of points which satisfy the equation of an elliptical curve is designated as the order of the curve. The first data object key constitutes a natural number, and the further second data object key, a point on the curve, is the result of multiplying the further first data object key by the curve point P of the elliptical curve.

The use of a cryptosystem on elliptical curves has the following advantages:
- the first data object key can be an arbitrary natural number from the interval $[1, n-1]$. Said number is not tied to any further functional conditions; the aspect of its arbitrariness will play a major part in the further progression.
- Breaking a cryptosystem on elliptical curves has a very high complexity that is much higher than in the case of RSA.
- The keys are very short in comparison with RSA and the calculations on the curve are relatively simple, as a result of which they can be implemented diversely and efficiently.
- The further second data object key can be calculated simply and at any time again from the further first data object key.

By means of the functions f and g, the further first data object key can be calculated very efficiently from the user identifier and the random value. It is thus possible to assign the cryptographic key pair to the chosen user identifier by means of mathematical functions. Owing to this functional relationship, it is not necessary here to keep a tabular assignment of key pair and a corresponding user identifier.

According to a further embodiment of the invention, the method comprises the step of the permissibility check of the first data object key. In the context of the permissibility check, a check is made to determine whether the further first data object key is greater than 1 and less than the order of the elliptical curve. If this check condition is met, the random value and also the further first and the further second data object keys are permissible. If the check condition is not met, however, a new random value is chosen, which is used to calculate anew the further first data object key and also to carry out anew the permissibility check of said data object key. This procedure is repeated until the permissibility check is passed.

The permissibility check can be extended by further check conditions, e.g. by the check to ascertain that the further first data object key has a high randomness. In this respect, it should be noted that cryptography usually employs algebraic structures containing only a finite number of elements. This is owing to the fact that, in the case of a finite number of elements, many problems that are innocuous in the real numbers become difficult, such that elliptical curves with a finite number of elements can be used effectively for cryptographic applications. For cryptographic applications it is then important that the algebraic structure used is large enough, that is to say that the number of points on an elliptical curve, designated as the order, is sufficiently large. In this context, it must be taken into consideration that the generated further first data object key can be greater than the order of the elliptical curve. In order nevertheless to enable an association here, it is customary to carry out a division of the further first data object key modulo the order of the elliptical curve. However, this gives rise to a high probability of the resultant number being in a lower range of values of the interval $[2, r-1]$ (where r is the order of the elliptical curve) or even 0 or 1, which thus reduces the difficulty of finding mathematically or by trial and error a point on the curve which lies in this range of values. Consequently, carrying out the permissibility check reliably prevents a limitation of the range of values in which the further first data object key is situated, and so the entropy of the further first data object key and thus the randomness thereof can thereby be ensured to a sufficient extent.

A further advantage of the permissibility check is that it can thereby be ensured that compatibility of the further first data object key with corresponding program libraries for elliptical curves, such as are available according to the prior art, can be reliably ensured.

It should be pointed out here that carrying out the permissibility check is not absolutely necessary in order to carry out the method for generating an asymmetrical cryptographic key pair using an elliptical curve function. Even without applying the permissibility check, it is possible here to generate key pairs which, however, under certain circumstances, depending on the user identifier and random value, cannot take account of very high security requirements which could be required for cryptographic applications. The permissibility check is, in the case of elliptical curves, a further step for ensuring that the generated key pairs satisfy precisely those security requirements.

According to one embodiment of the invention, the bit length of the random value is greater than or equal to the bit length of the order of the elliptical curve. Moreover, according to one embodiment of the invention, the random value is chosen such that the value of the generated further first data object key is less than the order of the elliptical curve. Both criteria likewise have, as already discussed for the permissibility check, the same effect, namely that a high entropy of the further first data object key can thus be ensured. Thus, in other words, the security of the further first data object key and thus the security of the encryption method are significantly increased.

According to one embodiment of the invention, the key pair is calculated for an RSA cryptosystem. An RSA cryptosystem is given by a number n, which is the product of two prime numbers p and q (n=p·q), the number d, which meets the condition gcd(d, (p−1)·(q−1))=1, and the number e, which meets the condition e·d≡1 mod (p−1)·(q−1) ("gcd" stands for greatest common divisor). After the choice of d and the calculation of e, the values p, q and (p−1)·(q−1) have to be erased. Which of the two numbers e and d is the public key and which is the private key can be chosen freely, in principle, in the case of RSA; in this invention, the functions f and g calculate the further first data object key d from the user identifier pw and the random value z. By means of the extended Euclidean algorithm, the further second data object key e is then calculated from the further first data object key d.

The advantages of the RSA method are the facts that the method is still very secure in the case of keys chosen with an appropriate length, and that it is widely used. However, RSA also has the disadvantages that it is slow in operation on account of the long key length required and modern factorization algorithms give cause to fear that RSA will be broke in the not too distant future.

For RSA, too, by means of the functions f and g it is possible to calculate the further first data object key from the user identifier and the random value. Thus, for RSA, too, it is possible to assign a cryptographic key pair to the chosen user identifier by means of mathematical functions. Owing to this functional relationship, it is not necessary to keep a tabular assignment of key pair and a corresponding user identifier for RSA, too.

According to a further aspect of the invention, the method comprises the step of the permissibility check of the first RSA data object key. In the context of the permissibility check, a check is made to determine whether the further first data object key d meets the conditions d lies in the interval [2, (p−1)·(q−1)−2] and
gcd (d, (p−1)·(q−1))=1.

If these check conditions are met, the random value and also the first and the further second data object keys are permissible. If the check condition is not met, however, a new random value z is chosen, which is used to calculate anew the further first data object key and to carry out anew the permissibility check of said data object key. This procedure is repeated until the permissibility check is passed.

According to a further embodiment of the invention, the random value is retrieved from a database, wherein the random value is uniquely assigned to the user identification. By way of example, upon first carrying out the method for generating the asymmetrical key pair, a random value is generated once by a trustworthy center, e.g. a certification authority, which value has to be indirectly accessible to a corresponding user in the case of the permissibility of the further first data object key for cryptographic operations. By storing the random value in a database, assigned to the unique user identification, it is possible for a computer program that executes the method for generating asymmetrical key pairs to retrieve the random value via a secure communication link on the basis of the user identification and to use it to generate the corresponding first and, if appropriate, also the further second data object key.

Preferably, the random value is stored in encrypted fashion in the database. For this purpose, according to one embodiment of the invention, it is possible to apply symmetrical encryption, e.g. using AES-256. The use of an encrypted random value has the advantage that dictionary attacks for decrypting the first key on a trial basis can thus be prevented.

According to a further embodiment of the invention, the computer program products are formed by applets or browser plug-ins. It is likewise possible to provide the computer program products as independent applications for a data processing system. The use of an applet or a browser plug-in has the advantage that it is not necessary to convert existing data processing systems for carrying out the method for key generation and in a consistent manner also for carrying out cryptographic operations such as encryption, decryption and also creation and verification of digital signatures: here it suffices merely to load an applet, for example via the internet, which can carry out the described operations in a secure manner.

According to a further embodiment of the invention, the further asymmetrical cryptographic key pair is received by a portable data carrier, wherein the ciphertext is stored on the portable data carrier. By way of example, the portable data carrier is a smart card, an identity document or a mobile telecommunication device such as a cellphone or a personal digital assistant (PDA).

In a further aspect, the invention relates to a computer program product comprising processor-executable instructions for carrying out method steps for decrypting a data object, wherein the data object can be decrypted by means of an initial first authorization key, wherein the initial first authorization key together with an initial second authorization key forms an initial asymmetrical cryptographic key pair, wherein the initial asymmetrical key pair is part of a key pair sequence. In this case, the method comprises the steps of accessing a first authorization key, wherein the first authorization key together with a second authorization key forms an asymmetrical cryptographic key pair, wherein the asymmetrical key pair is part of the key pair sequence. This is followed by retrieving a ciphertext, wherein the ciphertext is assigned to the asymmetrical cryptographic key pair, wherein the ciphertext comprises the initial first key encrypted with the second authorization key. This is followed by decrypting the encrypted initial first key with the first authorization key and decrypting the encrypted data object by means of the decrypted initial first key.

As already mentioned above, this method has the advantage that decryption of the encrypted data object can be carried out using an arbitrary asymmetrical key pair which is part of the key pair sequence. In this case, it is unimportant which asymmetrical key pair of the set of asymmetrical key pairs of the key pair sequence was previously used to encrypt the data object. Depending on the asymmetrical cryptographic key pair now used for decryption, a corresponding ciphertext is retrieved, by means of which the initial first key can be extracted, using which, finally, the data object can be decrypted.

According to a further embodiment of the invention, the computer program product furthermore comprises instructions for carrying out the step of receiving a key pair identifier assigned to the asymmetrical cryptographic key pair, wherein the ciphertext is retrieved on the basis of the key pair identifier. By way of example, the ciphertext is retrieved from a database. As an alternative thereto, it is possible, for example, for the asymmetrical key pair to be stored together with the ciphertext on a portable data carrier, such as, for example a smart card.

According to a further embodiment of the invention, the computer program product furthermore comprises instructions for carrying out the step of a signature check of the data object, wherein the signature check comprises the steps of reading a signature assigned to the data object, and verifying the signature of the data object, wherein the verification is effected with the second authorization key.

Carrying out an additional signature check in the case of a data object previously having been signed with the first authorization key has the advantage that it is thereby possible to verify that the data object has not been modified in an unauthorized manner since the original encryption operation.

According to a further embodiment of the invention, the data object is encrypted with a symmetrical data object key, wherein the symmetrical data object key is encrypted with the initial second authorization key, wherein decrypting the encrypted data object in this case comprises the further step of decrypting the encrypted symmetrical data object key with the decrypted initial first authorization key and decrypting the encrypted data object with the decrypted symmetrical key.

According to a further embodiment of the invention, accessing the first authorization key comprises the step of receiving a user identification and a user identifier assigned to the user identification. This is followed by retrieving a random value assigned to the user identification from a further database, and calculating the first authorization key, wherein the random value and the user identifier are included in the calculation.

According to a further embodiment of the invention, the signature check furthermore comprises the step of calculating the second authorization key from the first authorization key by means of an asymmetrical cryptographic key generating method, wherein the first and the second authorization keys form the asymmetrical cryptographic key pair.

According to a further embodiment of the invention, the random value is retrieved from the further database via a secure communication link. In this case, it is possible for the database from which the ciphertext is retrieved and from which the random value is retrieved to be identical.

According to a further embodiment of the invention, the random value is stored in encrypted fashion in the further database.

According to a further embodiment of the invention, the data object is a medical data object.

In a further aspect, the invention relates to a computer program product comprising processor-executable instructions for carrying out method steps for generating a digital signature of a data object, wherein the method comprises receiving the user identification and a user identifier assigned to the user identification. Furthermore, the method comprises retrieving a random value assigned to the user identification from a second database. This is followed by calculating a further first data object key, wherein the random value and the user identifier are included in the calculation, wherein the further first and the further second data object keys form an asymmetrical cryptographic key pair. The calculation of the further first data object key is followed by the generation of the digital signature, which is influenced by the further first data object key and, for example, the cryptographic hash value of the data object. The digital signature is stored together with the identifier of the data object in the first database.

In a further aspect, the invention relates to a data processing system for providing authorization keys, wherein the data processing system comprises means for receiving a further asymmetrical cryptographic key pair, wherein the further asymmetrical key pair is part of a key pair sequence, wherein the further asymmetrical key pair comprises a further first and a further second authorization key. The data processing system furthermore comprises means for retrieving a ciphertext, wherein the ciphertext is assigned to the key pair which immediately precedes the further key pair in the sequence of key pairs, wherein the ciphertext comprises the initial first key encrypted with the second authorization key of the key pair which immediately precedes the further key pair in the sequence of key pairs. The data processing system further-more comprises means for encrypting the initial first authorization key with the first authorization key of the key pair which immediately precedes the further key pair in the sequence of key pairs, and means for generating a further ciphertext by encrypting the decrypted initial first authorization key with the second authorization key of the further key pair. Furthermore, the data processing system comprises means for storing the further ciphertext.

Preferably, the data processing system is a data processing system of a trustworthy center, e.g. of a certification authority or of a trust center. As an alternative, it is also possible to provide a corresponding, preferably portable, hardware unit which comprises the data processing system as a trustworthy center. In a further alternative, the trustworthy center can be the client itself that performs the cryptographic operations.

According to a further embodiment of the invention, the data processing system is a data processing system that runs on a separate, secured hardware module. By way of example a trusted platform module (TPM) can be used in this case.

BRIEF DESCRIPTION OF THE DRAWINGS

Embodiments of the invention are explained in greater detail below with reference to drawings, in which.

DETAILED DESCRIPTION OF THE INVENTION

Figure 1:
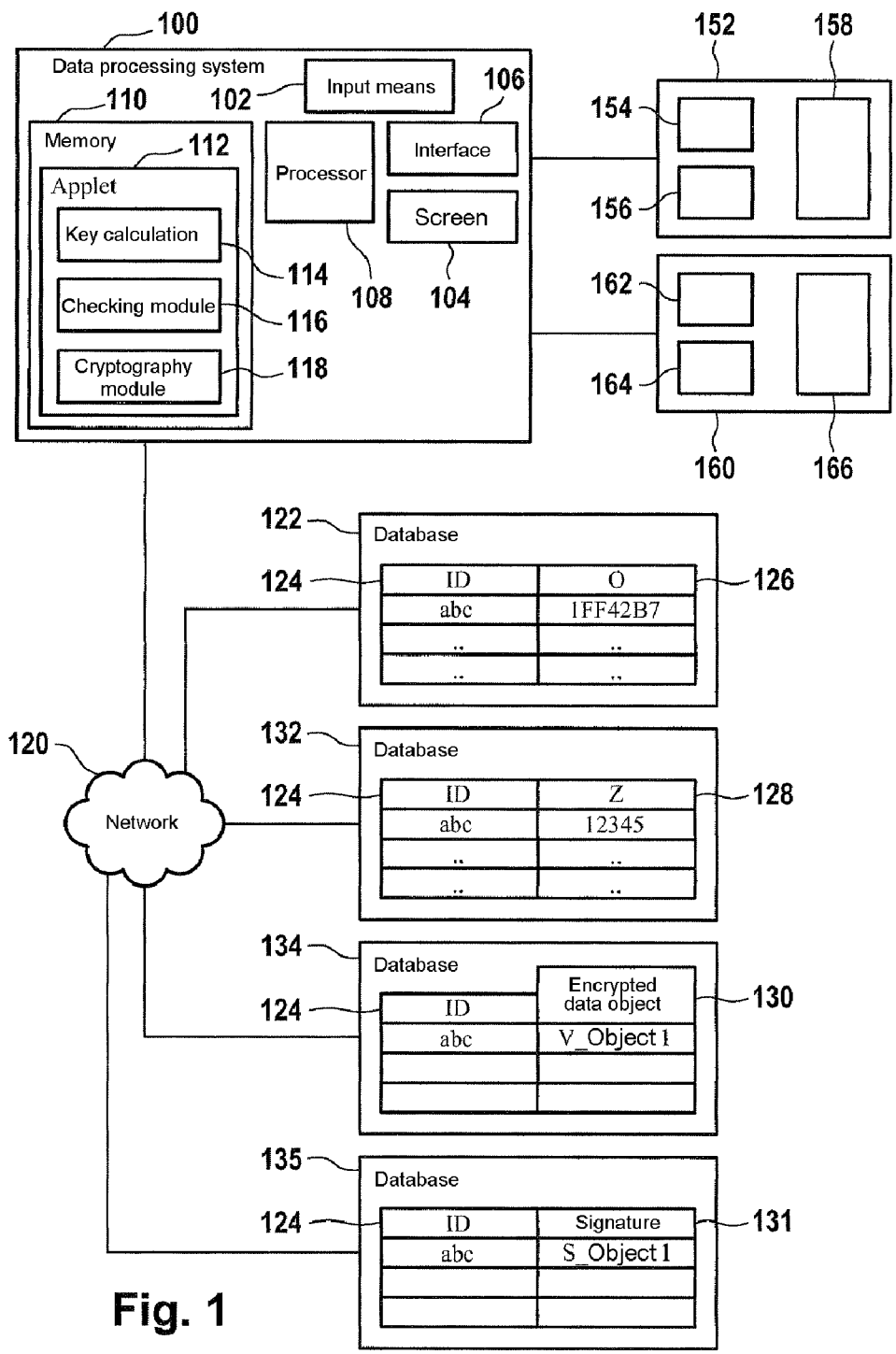
FIG. 1 shows a block diagram of a data processing system.

FIG. 1 shows a data processing system 100. The data processing system comprises input means 102, such as, for example, a keyboard, a mouse, a PIN pad, means for detecting biometric features, such as, for example, a fingerprint scanner or an iris scanner. Furthermore, the data processing system 100 comprises a screen 104 and also an interface 106, which can be used for example for communication with a network 120, such as the internet. Furthermore, the data processing system 100 comprises a processor 108, which is designed to execute executable instructions for carrying out method steps. Said instructions are contained for example in the form of an applet 112 in the memory 110.

By way of example the data processing system 100 can be used for generating asymmetric cryptographic key pairs and for subsequently encrypting and decrypting data objects and also for generating and verifying digital signatures and for further cryptographic operations. This firstly requires a calculation of key pairs, which can be effected for example by means of the module 114 of the applet 112. For calculating keys, in this case, by means of the module 114 the following procedure is adopted: firstly, a user identifier that can be chosen as desired is obtained from a user via the input means 102. A first data object key is thereupon calculated from the user identifier, wherein a random value, generated by the data processing system 100, and the user identifier are included in the calculation. The first data object key calculated here is a private key of the user, wherein it is possible that, in order to use the first data object key in cryptographic applications, additional parameters have to be concomitantly published in order to utilize the first data object key for carrying out cryptographic operations. As already noted above, in the case of elliptical curves, it is necessary, in addition to the first and second data object keys, also to make available the domain parameters of the elliptical curve, which in combination with the first and second data object keys makes possible the application of cryptographic operations. For RSA it similarly holds true that the natural number n has to be concomitantly published in order to be able to carry out cryptographic operations.

Calculation of the first data object key is followed by a check of the data object key by means of the checking module 116. This check serves to check the permissibility of the first data object key, namely whether the generated first data object key satisfies various security aspects.

By way of example, in the case of elliptical curves, the public key, that is to say the second data object key, is calculated from the first private data object key by a curved point on an elliptical curve being multiplied by the secret key. In this case, the permissibility check of the first data object key consists in checking whether the first data object key is greater than one and less than the order of the elliptical curve, wherein, if this check condition is met, the random value and the first and second data object keys are permissible. If this is not the case, however, it is necessary to calculate a new first data object key and, consequently, also a new second data object key by choosing a new random value and repeatedly carrying out the method for key calculation by means of the module 114 and also the method for checking the generated keys by means of the module 116.

The random value used for key calculation is thereupon stored in a database 132 and, if appropriate, encrypted. This is effected, for example, such that a unique user identification is allocated for the corresponding user, wherein the previously generated random value 128 is assigned to this user identification 124 in a table of the database 132. In the present example in FIG. 1, the random value Z having the value "12345" is assigned to the user identifier "abc". As already mentioned above, here the random value is preferably stored in encrypted form in the database 132 in order reliably to prevent dictionary attacks on the first data object key.

In a further database 122, the public key 126 generated by means of the key calculation module 114 is likewise stored in a manner assigned to the user identification 124. By way of example, the public key "1FF42B7" is again assigned to the user identification "abc".

It should be assumed hereinafter that a data object 130 likewise assigned to the user identification 124 is stored in an encrypted manner in a database 134. In this case, the data object is encrypted with the public key 126 stored in the database 122. For decrypting the data object 130, the following procedure is then adopted: via the input means 102, a user inputs their user identification and the user identifier chosen in the user identification. By means of the module 114, the calculation of the first data object key is thereupon effected using the random value 128, which is retrieved from the database 132 on the basis of the user identification 124. As already mentioned above, the random value 128 and the user identifier previously input into the data processing system via the input means 102 are included in this calculation of the first data object key.

By means of the secret and private data object key then generated in this way, it is then possible to decrypt the data object 130.

At least one signature 131 S_Object 1 of the data object and also optionally the data object 130 itself can be stored in a database 135. In this case, the data object 130 is signed with the secret key assigned to the public key 126. The signature is correspondingly verified with the public key 126.

It should be noted at this juncture that the user identifier that can be chosen as desired and is input into the data processing system 100 via the input means 102 can be, for example, a number combination, a number-letter combination or else a biometric feature. By way of example, in the case where a biometric feature is used, a bit sequence can be calculated uniquely from the biometric data, which bit sequence can thereupon be included as user identifier in the key calculation by means of the module 114.

Furthermore, it should be noted that, in particular during the encryption and decryption of medical data objects by means of the data processing system 100, for example, the following procedure is adopted: via the interface 106, for example, a medical data object is received from an imaging medical instrument such as an X-ray device. X-ray data are typically image data constituting extensive volumes of data. The data processing system generates a random symmetrical key, with which these medical X-ray data are encrypted. These encrypted data are thereupon stored in the database 134 in a manner associated with the unique user identification 124. The generated symmetrical key is thereupon encrypted with the public key 126. This symmetrical key encrypted in this way is likewise stored in the database 134 in the manner associated with the user identification 124 and the encrypted data.

For decryption, the encrypted symmetrical key is then decrypted by means of the cryptography module 118 by a procedure in which the corresponding private key is generated using the user identifier as described above and is used for the decryption. With the symmetrical key thus obtained, it is thereupon possible to decrypt the encrypted data object 130.

Preferably, data objects 130 are stored in each case individually in an encrypted manner in the database 134. Even in the case of a set of semantically associated data objects, preferably each individual data object per se is stored in an encrypted manner in the database 134, such that, in the case of retrieval of an individual data object, this encrypted data object 130 is transmitted to the data processing system 100, whereupon it is decrypted there. If, in contrast thereto, for semantically associated data objects that would be combined in a single data, encrypted and stored, for reasons of minimizing the data volume to be transported, the decryption were performed in the database, then the operator would have access to the decrypted data objects. By contrast, the procedure described above has the advantage that at no time does the database 134, or the operator thereof, require access to decrypted keys or data objects.

The data processing system 100 is furthermore designed to provide authorization keys in a hierarchical manner and to use them for processes of encrypting and decrypting data objects. Without restricting the generality, it should be assumed hereinafter that, for example, a user is in possession of a smart card 152, on which a private authorization key 154 and a public authorization key 156 are stored. If a new data object is then intended to be encrypted, for this purpose it is possible to employ the above-described method using an additional symmetrical key, with which a data object is encrypted. The data object 130 encrypted with the symmetrical key in this way is stored in a manner associated together with the unique user identification 124 in the database 134.

In a departure from the above description, however, according to a further embodiment of the invention, the symmetrical key is then encrypted with an initial public key stored as initial public key 126 in the database 122, for example. Moreover, by way of example, a ciphertext 150 is likewise stored in the database 122. Said ciphertext 150 can in this case be assigned uniquely to the smart card 152.

If such a process of encryption of the abovementioned symmetrical key then takes place, firstly the initial authorization key in the form of a public key 126 assigned to the unique user identification 124 is retrieved from the database 122. By means of the cryptography module 118, the symmetrical key is thereupon encrypted with the initial public authorization key. This encrypted symmetrical key is thereupon stored in a manner associated with the encrypted data object 130 in the database 134.

A process of decryption of the encrypted data object 130 requires decryption of the symmetrical data object key. This requires knowledge of the private initial authorization key, which together with the initial public authorization key forms an asymmetrical cryptographic key pair. The ciphertext 150 assigned to the smart card 152 then serves for obtaining the private initial authorization key. The ciphertext contains, in an encrypted manner, the initial private authorization key which was previously encrypted with the public authorization key 156 of the smart card 152. Using the interface 106, the cryptography module 118 is then able to extract the initial private authorization key from the ciphertext 150 using the private authorization key 154 of the smart card 152. By means of said initial private authorization key, the cryptography module 118 is thereupon able to decrypt the encrypted symmetrical key associated with the encrypted data object 130, in order thereupon to decrypt the encrypted data object 130 itself with the symmetrical key thus obtained.

It should now be assumed that a user of the smart card 152 would like to replace said smart card by a new smart card 160, or would like to use, alongside the smart card 152, an additional smart card 160 for carrying out processes of encrypting and decrypting data objects. This requires a hierarchical provision of authorization keys, which takes place as follows:

It should be assumed that a new private authorization key 162 and a new public authorization key 164 are already situated on the smart card 160. It should be noted here that this presence of authorization keys 162 and 164 on a smart card 160 can readily be replaced by the above-described method for generating data object keys which are input into the data processing system 100 by means of a user identifier that can be chosen as desired. In the latter case, the smart card 160 would be omitted—data object keys would be provided using said user identifier by means of the data processing system 100 itself. It should be assumed below, however, that, without restricting the generality, a user would additionally like to employ the smart card 160 with the authorization keys 162 and 164. For this purpose, according to one preferred embodiment of the invention, either the smart cards 152 and 160 are introduced into a corresponding reader of the data processing system 100 in an order specified by the data processing system by means of the screen, or else the data processing system 100 is able to read both smart cards 152 and 160 simultaneously. It should be assumed hereinafter that simultaneous access to the smart cards 152 and 160 is possible.

After a user has introduced the two smart cards 152 and 160 into corresponding readers of the data processing system 100, the data processing system 100 reads out the ciphertext 150 from the database 122, which ciphertext was assigned to the "old smart card" 152. As already described in detail above, the data processing system 100 is thus able to extract the initial private authorization key from the ciphertext using the private authorization key 154. The initial private authorization key thus obtained is thereupon encrypted with the public authorization key 164 of the new smart card 160. This encrypted initial authorization key in turn forms a new ciphertext 150, which is stored in a manner associated with the smart card 160 in the database 122. In this case, the ciphertext calculation is effected by means of the module 114.

Data are then encrypted, as described in detail above, using the symmetrical key which, in principle, independently of the use of the smart card 152 or 160, is encrypted with the initial public key 126 and is stored in a manner associated with the corresponding encrypted data object 130 in the database 134. If a process of decryption of an encrypted data object 130 is then effected in the opposite order, this can be effected using either the smart card 152 or the smart card 160. In both cases, the private key 154 or 162 respectively assigned to the smart card is used in order to decrypt the ciphertext assigned to the smart card respectively used. The initial private key thus obtained can then in turn be used to perform a process of decryption of the symmetrical data object key stored in a manner associated with the encrypted data object 130 in the database 134.

It should be pointed out here that, preferably, the private keys 154 and 162 never leave the smart cards 152 and 160. For this reason, the smart cards 152 and 160 have corresponding hardware or software modules 158 and 166, respectively, which can be used to perform corresponding cryptography processes such as, for example, processes of decrypting the ciphertext 150. Likewise, encryption of the initial private key should preferably be effected in the modules 158 and respectively 166 themselves, such that the initial first authorization key extracted by the smart cards 152 and 160 never leaves said smart cards, such that misuse of the initial private authorization key is precluded.

Figure 2:
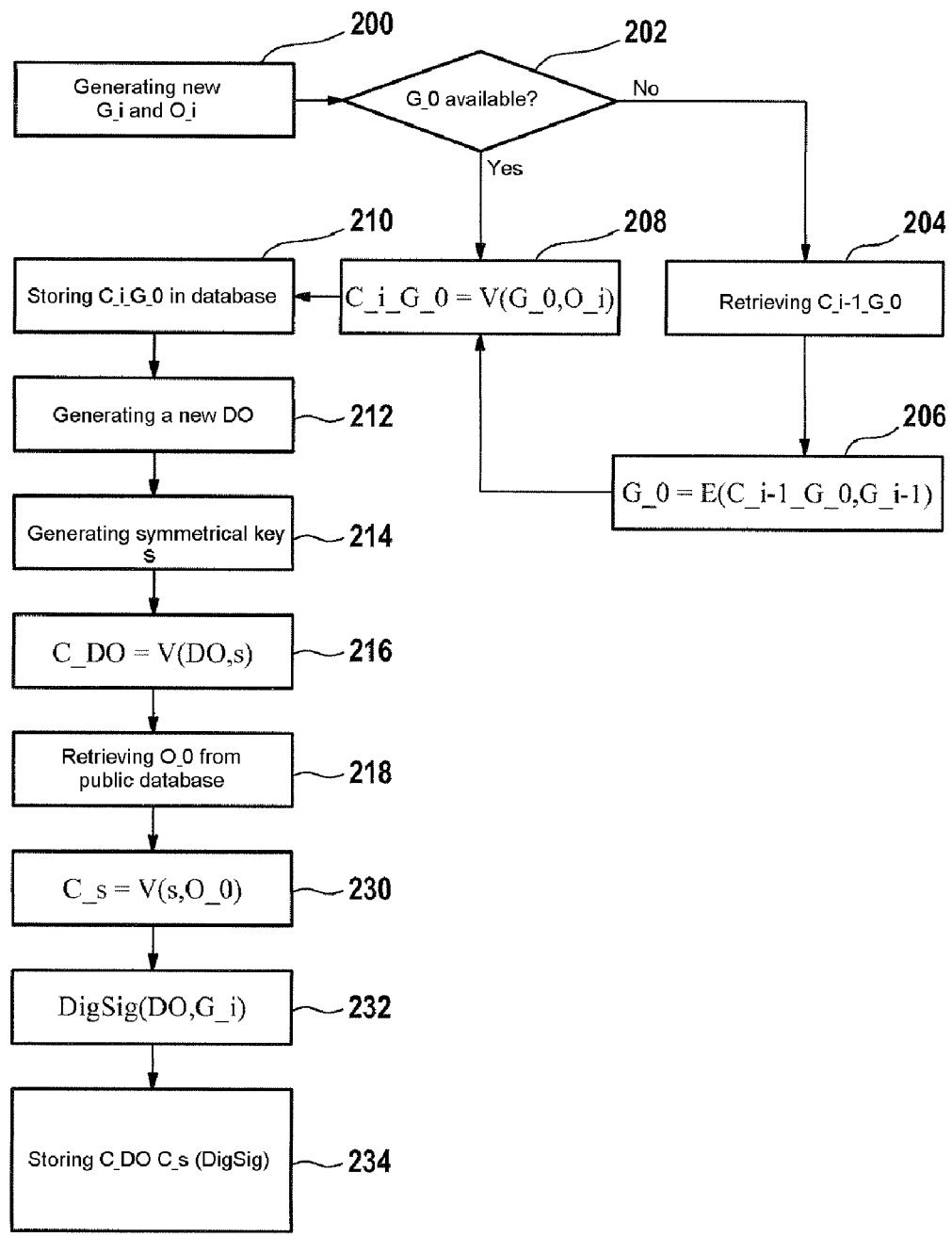
FIG. 2 shows a flowchart of a method for providing authorization keys and for encrypting data.

FIG. 2 shows a method for carrying out method steps for providing authorization keys and for encrypting a data object. The method begins in step 200, in which a new private key $G_i$ and public key $O_i$ are generated. This can be done, for example, by the choice of a new user identifier as described above or by the provision of a new smart card, in which a new private authorization key $G_i$ and a new public authorization key $O_i$ have already been stored. Step 202 involves checking whether an initial private authorization key with index i=0 is available. This will typically be the case only when no further asymmetrical cryptographic key pairs have previously been generated apart from the initial private authorization key and the associated initial public authorization key. However, once again without restricting the generality, here it should also be assumed below that a set of different asymmetrical key pairs which are part of a key pair sequence already exists. Accordingly, at the time of the generation of the private key $G_i$ and the public key $O_i$, overall further asymmetrical cryptographic key pairs exist in addition to the initial key pair i−1.

It should be assumed that the initial private authorization key with index 0 $G_0$ is not available, and so step 202 is followed by step 204, in which a ciphertext assigned to the smart card with index i−1 is retrieved from a database. Alternatively, it is also possible for said ciphertext to be stored on the smart card assigned to the index i−1.

In step 206, the ciphertext is thereupon encrypted using the private authorization key of the smart card with index i−1. As a result of the decryption of the ciphertext, the initial private authorization key is obtained in step 206. Said initial private authorization key $G_0$ is thereupon encrypted anew in step 208, wherein encryption takes place here using the new public key $O_i$. In step 210, the new ciphertext thus obtained is stored in a manner assigned to the new smart card in a database.

The direct transition from step 202 to 208 is usually necessary only when the new smart card with the keys $G_i$ and $O_i$ is the smart card with index i=1.

After a hierarchical provision of authorization keys has been effected in steps 200 to 210, a process of encryption of data objects ensues in steps 212 to 234. In other words, steps 200 to 210 only have to be carried out once when a new smart card with new asymmetrical keys is issued, where steps 212 to 234 have to be carried out for each process of encryption of data objects.

In step 212, a new data object is then generated. In step 214, this is followed by the generation of a symmetrical key s, which is used in step 216 to encrypt the data object from step 212. In step 218, the initial public authorization key $O_0$ is retrieved from a public database, wherein, in step 230, said initial public authorization key is used to encrypt the symmetrical key that was obtained in step 214.

Finally, the encrypted data object and the encrypted symmetrical key are stored in a corresponding patient database in step 234.

Step 232, succeeding step 230, is an optional step in which there is the possibility of additionally signing the data object in order thus to prevent unauthorized misuse and manipulation of the data object. Such digital signing is preferably effected with the private authorization key $G_i$ of the smart card currently being used. If step 232 was carried out, the digital signature is additionally stored together with the encrypted data object and the encrypted symmetrical key in step 234.

Figure 3:
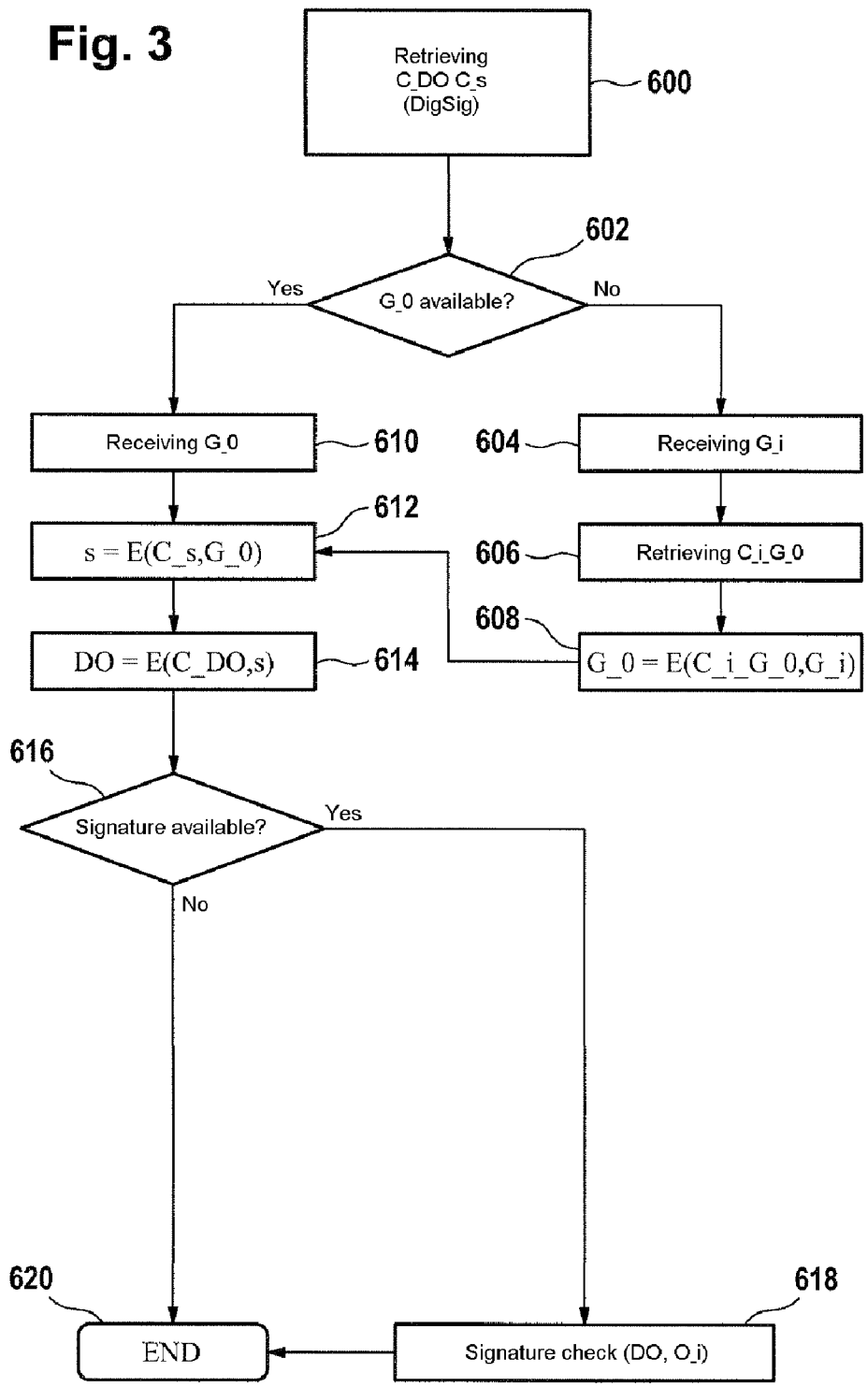
FIG. 3 shows a flowchart of a method for decrypting data.

FIG. 3 shows a flowchart for decrypting data objects. It should be assumed below that a digital signature was added to the data object. Thus, in step 600, the encrypted data object, the encrypted symmetrical key and the digital signature are retrieved. Step 602 involves checking whether the initial private authorization key is available. This may be the case for example when, apart from the initial authorization key, no further keys were output in a sequence. If this is the case, said initial private authorization key is received in step 610 and the encrypted symmetrical data object key is decrypted by means of the initial private authorization key in step 612. This is possible since the symmetrical data object key s was previously encrypted with the initial public authorization key $O_0$; in this respect, cf. step 230 in FIG. 2.

After the symmetrical key has been decrypted in step 612, in step 614 this is followed by decryption of the data object with the symmetrical key s thus obtained. Step 616 involves checking whether a signature is available for the data object. If this is the case, in step 618 a signature check is effected using the public authorization key of the smart card which was originally used for signing the data object. This does not necessarily require the presence of said smart card itself, since the public authorization key of said smart card can readily be stored on a public server.

If it emerges in step 602 that the initial private authorization key is not available, typically because a sequence of additional authorization keys has already been provided, the method is continued in step 604 using an arbitrary one of these authorization key pairs which are presently available. It should be assumed below that the authorization key pair with index i is involved in this case. The authorization key pair with index i comprises a private authorization key $G_i$ received in step 604. Afterward, in step 606, either a corresponding ciphertext $C_{i\_G0}$ assigned to said index is retrieved from the smart card itself which is the carrier of the private authorization key i, or said ciphertext is retrieved from an external database in step 606. In step 608, said ciphertext is thereupon decrypted with the private authorization key $G_i$ received in step 604. As a result, the initial private authorization key $G_0$ is obtained in step 608. Said initial private authorization key $G_0$ can thereupon be used in step 612 to decrypt the encrypted symmetrical key. Afterward, as already discussed, steps 614 to 620 ensue, wherein the method ends in step 620.

It should also be noted here that in steps 610 and 604 mention is made of "receiving" private keys. However, this is not intended to be understood such that transmission of the private keys via a medium, such as a network, for example, takes place. Rather, steps 604 to 612 or 610 and 612 should preferably be effected on a smart card or in a data processing system itself, without an unauthorized user being able to intercept or read out $G_0$ or $G_i$ in any way.

Figure 4:
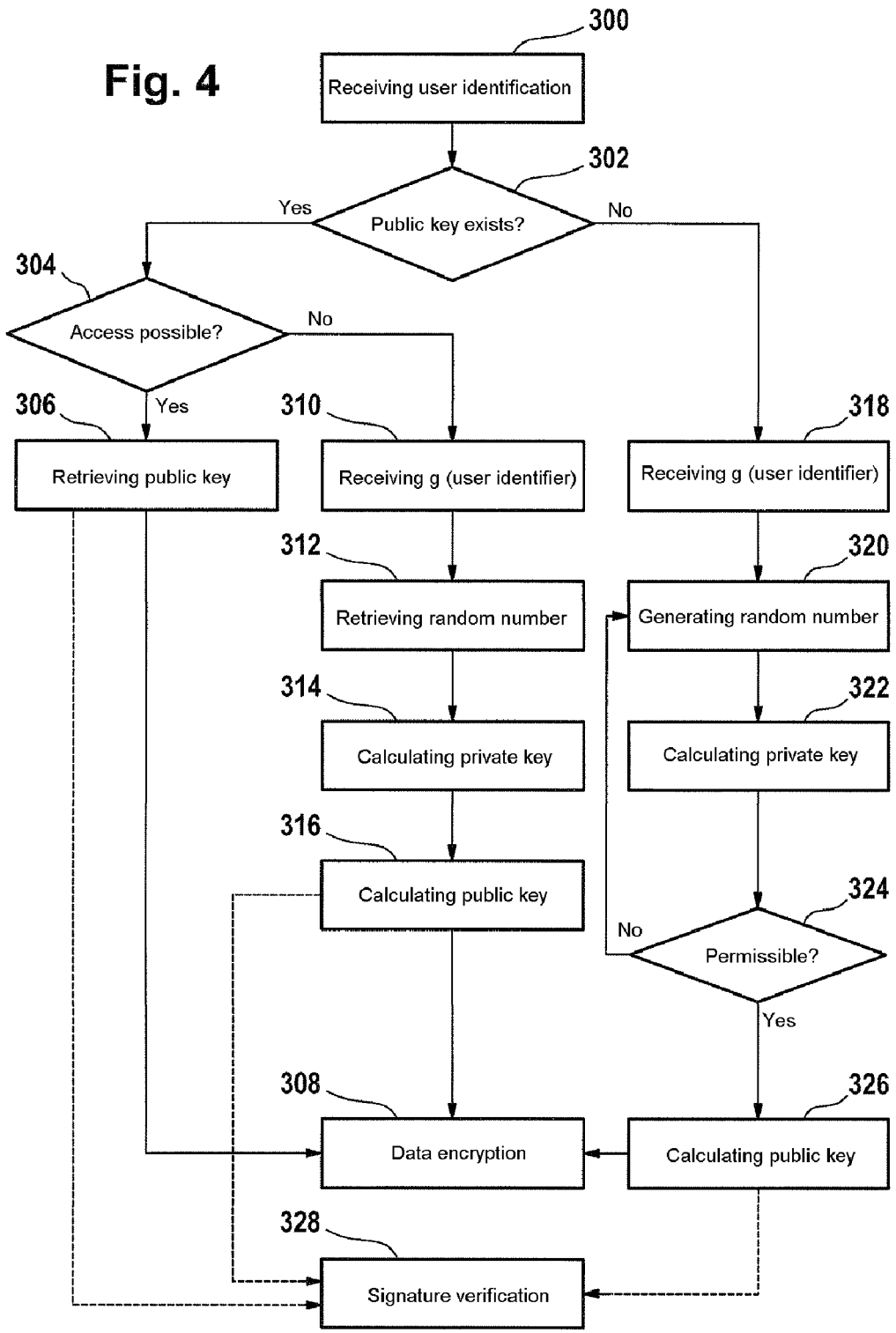
FIG. 4 shows a flowchart of a method for asymmetrically encrypting data.

FIG. 4 shows the method for generating an asymmetrical key pair and its exemplary use for encrypting data objects and for verifying digital signatures of data objects. In step 300, a unique user identification is received. In step 302, this is followed by a check to determine whether a public key exists which is assigned to the user identification received in step 300. If this is the case, step 304 involves checking whether access to this public key is possible. If this is possible, in step 306 the public key is retrieved, and the data object can be encrypted by means of the public key for example in step 308 or the digital signature of a data object can be verified in step 328.

By contrast, if the check in step 304 reveals that access to the public key is not possible, then the public key has to be generated. This is done beginning with step 310, in which either a freely selectable user identifier is received and the function g is applied to said user identifier or the value g (user identifier) is already received. This is followed by step 312, in which a random value is retrieved from a corresponding database on the basis of the user identification. By applying the function f to the random value and g (user identifier), the calculation of the private key is effected in step 314. Finally, in step 316, the public key is calculated from the private key, wherein the private key and the public key form an asymmetrical cryptographic key pair.

The calculation of the public key in step 316 is effected in the case of elliptical curves, for example, by the public key being calculated by multiplication of the private key by a curve point of an elliptical curve. In this case, a portion of the domain parameters used for generating the public key has to be known to the user of the encryption method in FIG. 3.

Calculation of the public key in step 316 is in turn followed by encryption of the data object by means of the public key in step 308 or verification of a digital signature of a data object in step 328.

If it emerges in the checking step 302 that no public key exists, then this requires initial generation of an asymmetrical key pair. This is done by a procedure in which, in step 318, either a freely selectable user identifier is received and the function g is applied to said user identifier or the value g (user identifier) is already received.

In step 320, a random number is thereupon generated, whereupon in step 322, as already described for step 314, a candidate for a private key is generated by applying the function f to g (user identifier) and the random number.

In step 324, a permissibility check is effected, which, in the case of the elliptical curve method, for example, consists of the check to determine whether the private data object key is greater than 1 and less than the order of the elliptical curve. If the permissibility check is passed, then the random value and also the private key are permissible in step 324. The calculation of the public key can thereupon be carried out in step 326, whereupon, for example, the data encryption is effected in step 308 or the verification of the digital signature is effected in step 328.

By contrast, if it emerges in step 324 that the candidate calculated in step 322 is not permissible for a private data object key, then a random number is generated anew in step 320, whereupon steps 322 and 324 are again carried out. This is done until the permissibility check in step 324 is successful, whereupon step 326 comprising the calculation of the public key and, for example step 308 comprising the data encryption or step 328 comprising the verification of the digital signature are carried out.

Figure 5:
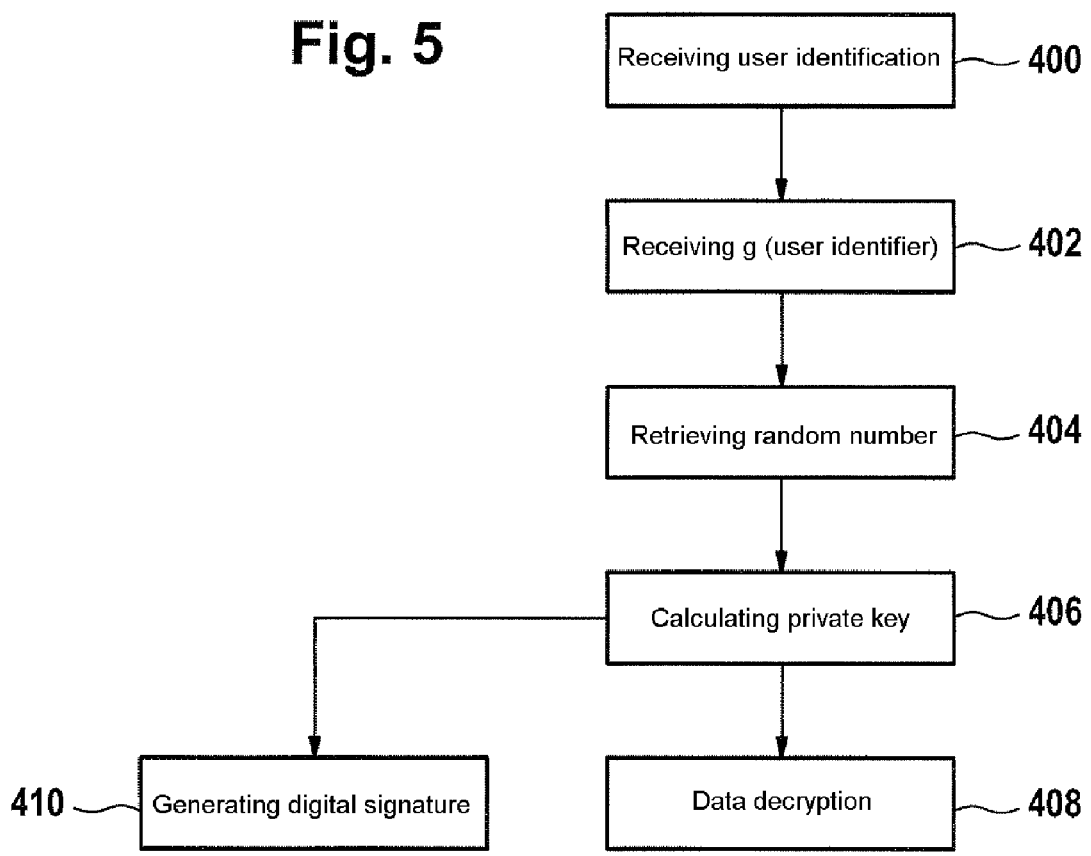
FIG. 5 shows a flowchart of a method for decrypting data by means of an asymmetrical key method.

In FIG. 5 it is then assumed that, as shown in FIG. 4, the private key was calculated in step 322 and the public key was calculated in step 326 for example using an elliptical curve. FIG. 5 shows a method for decrypting a data object. The method begins in turn with step 400, reception of a unique user identification. Moreover, a HASH value of a user identifier is thereupon received in step 402. Using the user identification, a random number is retrieved from an external database in step 404, from which a private key can be calculated using the HASH value of the user identifier in step 406. Said private key can then be used to decrypt, in step 408, the data encrypted with the public data object key.

Figure 6:
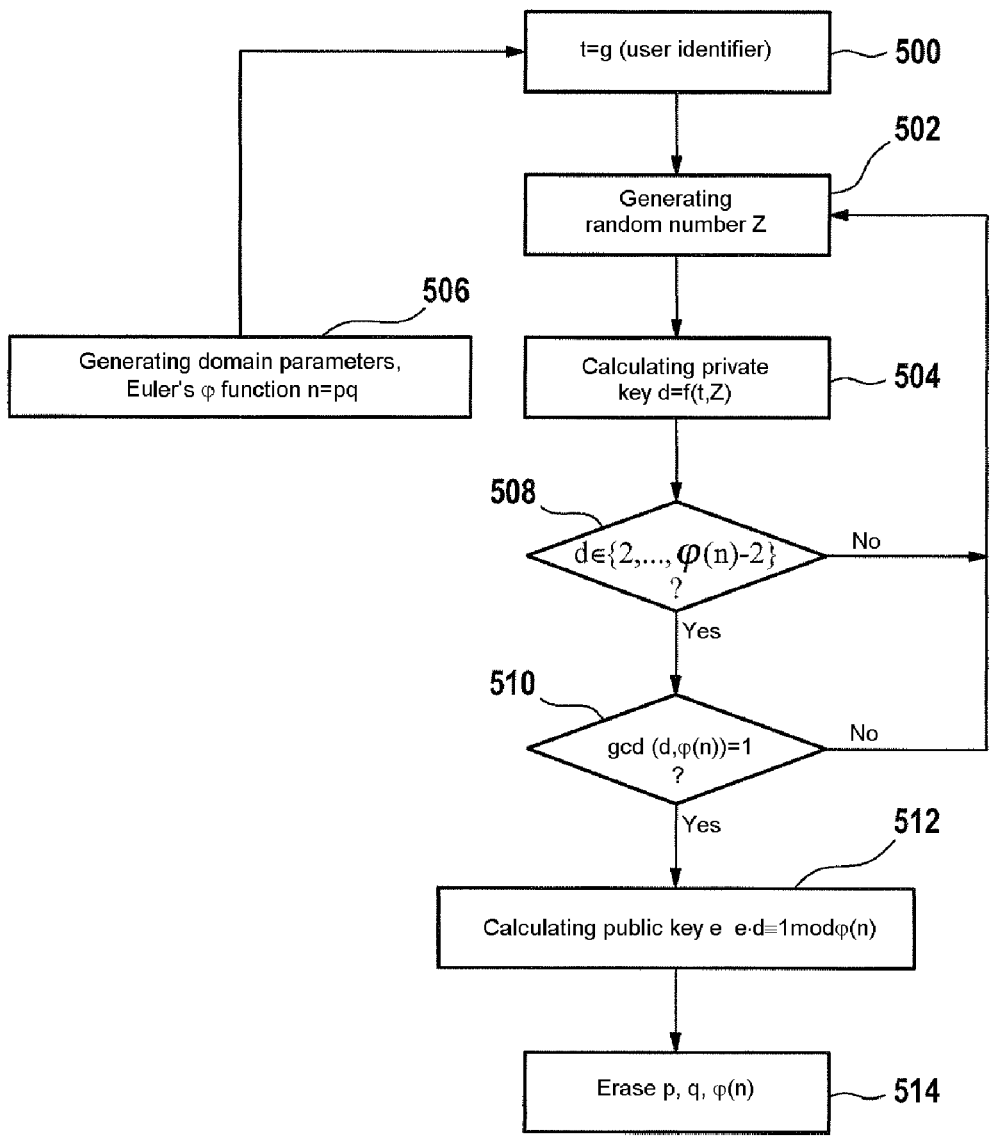
FIG. 6 shows a flowchart of a method for calculating asymmetrical keys according to the RSA method.

FIG. 6 shows a flowchart of a method for calculating an asymmetrical key pair according to the RSA method. The method begins with step 506, which involves choosing two prime numbers p and q in accordance with the current security requirements for RSA. The two numbers are multiplied together and the result is called n. Euler's φ function is subsequently applied to n, such that the value φ(n) is obtained.

In the subsequent step 500, a user identifier is received, to which the function g is applied, or the function value g (user identifier) is received directly. This is followed by step 502, in which a random value is generated. By applying the function f to the random value and g (user identifier), the calculation of a candidate for the private key d is effected in step 504.

A permissibility check is effected in step 508, wherein the permissibility check proceeds in a plurality of stages in the case of the RSA method. Thus, firstly step 508 involves checking whether d lies in the interval [2, φ(n)–2].

If the checking step 508 reveals that the check condition is not met, the method jumps back to step 502, where a new random value is generated. This is in turn followed by step 504 with the renewed calculation of a candidate for the private key e on the basis of the new random value and the renewed checking of the candidate d in step 508. This loop of steps 502, 504 and 508 is repeated until the check condition is met in step 508. It is only then that the method continues with step 510.

Step 510 comprises a further checking step, namely whether φ(n) and the key candidate d are relatively prime, i.e. gcd(d, φ(n))=1. If this is not the case, the method again jumps back to step 502 and a new random value is generated, followed by steps 504, 508, 510. This loop of steps 502, 504, 508 and 510 is also repeated until the check condition is met in step 510. It is only then the method continues with step 512. Preferably, the checking step 508 is carried out before the checking step 510 since the computational complexity for step 508 is significantly lower than the computational complexity for step 510.

In step 512, finally, the public key e is calculated, such that e satisfies the congruence relationship e·d≡1 mod φ(n) where e∈[1, φ(n)–1]. In order to use the private key d in cryptographic methods, it is also necessary for n to be disclosed.

In the final step 514, the numbers p, q and φ(n) are discarded, i.e. erased.

Further checking steps can be employed alongside the checking steps 508 and 510 in order thus to increase the security of the asymmetrical key pair generated.

Figure 7:
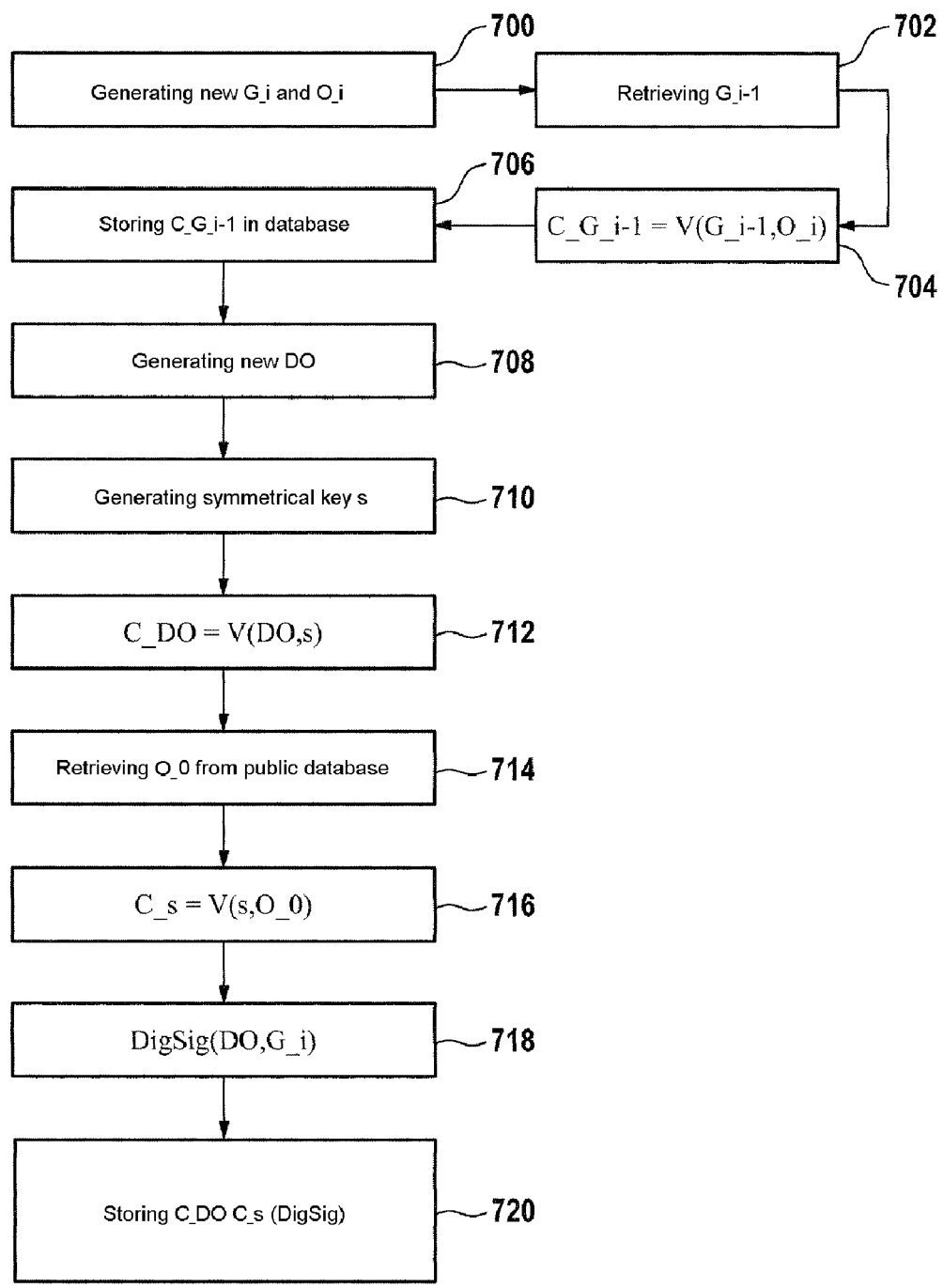
FIG. 7 shows a further flowchart of a method for hierarchically providing authorization keys and for encrypting data.

FIG. 7 shows a further flowchart of a method for hierarchically providing authorization keys and for encrypting data. The method begins in step 700, in which a new private key Gi and a new public key Oi are generated. In this case, the new private key Gi and the public key Oi can be stored on a new smart card. Step 702 thereupon involves retrieving a private key Gi–1 which, in the sequence of authorization keys, immediately precedes the pair of authorization keys which was generated in step 700. In a practical example of smart cards, in step 700 the new key pair Gi and Oi would be retrieved from a new smart card, whereas in step 702 the private predecessor authorization key Gi–1 is retrieved from a predecessor smart card. Step 704 thereupon involves encrypting this private predecessor key Gi–1 with the public key Oi of the new smart card. The resulting ciphertext is stored in a database in step 706.

After a hierarchical provision of authorization keys has been effected in steps 700 to 706, a process of encryption of data objects ensues in steps 708 to 720. In other words, steps 700 to 706 only have to be carried out once when a new smart card with new asymmetrical keys Gi and Oi is issued, whereas steps 708 to 720 have to be carried out for each process of encryption of data objects. A new data object is then generated in step 708. Step 710 thereupon involves generating a symmetrical key s, which is used in step 712 to encrypt the data object from step 708. In step 714, the initial public authorization key O0 is retrieved from a public database, wherein in step 716 said initial public authorization key is used for encrypting the symmetrical key s that was obtained in step 710.

Finally, the encrypted data object and the encrypted symmetrical key are stored in a corresponding patient database in step 720.

Step 718, succeeding step 716, is an optional step in which there is the possibility of additionally signing the data object in order thus to prevent unauthorized misuse and manipulation of the data object. Such digital signing is preferably effected with the private authorization key Gi of the smart card currently being used. If step 718 was carried out, the digital signature is additionally stored together with the encrypted data object and the encrypted symmetrical key in step 720.

Figure 8:
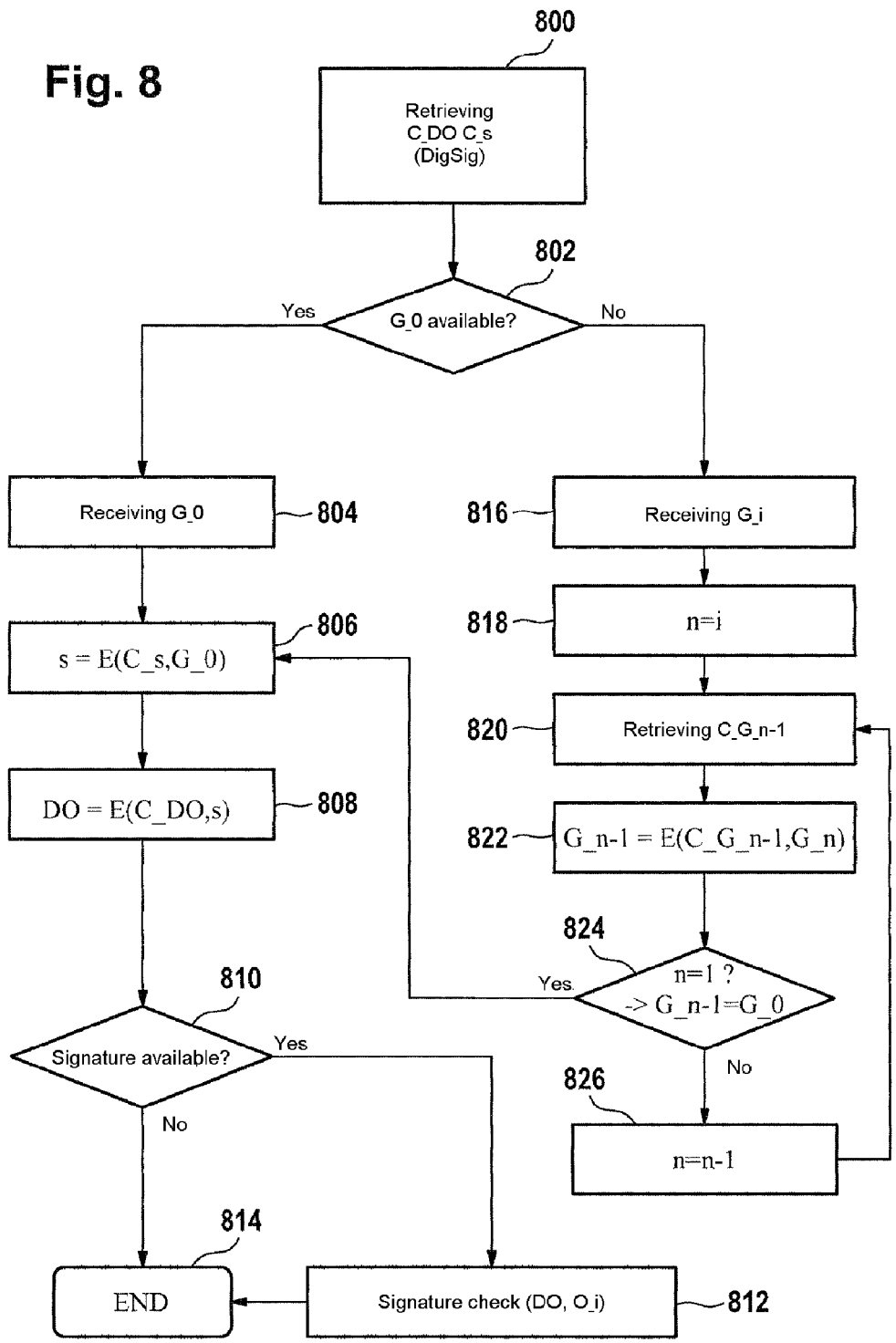
FIG. 8 shows a further flowchart for decrypting data objects.

FIG. 8 shows a further flowchart for decrypting data objects. It should be assumed below that a digital signature was added to the data object. Thus, the encrypted data object, the encrypted symmetrical key and the digital signature are retrieved in step 800. Step 802 involves checking whether the initial private authorization key is available. This may be the case, for example, when, apart from the initial authorization key, no further keys have been output in a hierarchical sequence. If this is the case, said initial private authorization key G0 is received in step 804 and the encrypted symmetrical data object key is decrypted by means of the initial private authorization key G0 in step 806. This is possible in that the symmetrical data object key s was previously encrypted with the initial public authorization key O_0; in this respect, cf. step 716 in FIG. 7.

After the symmetrical key has been decrypted in step 806, step 808 thereupon involves encrypting the data object with the symmetrical key s thus obtained. Step 810 involves checking whether a signature is available for the data object. If this is the case, in step 812 a signature check is effected using the public authorization key of the smart card which was originally used for signing the data object. This does not necessarily require the presence of said smart card itself, since the public authorization key of said smart card can readily be stored on a public server.

If it emerges in step 802 that the initial authorization key is not directly available, typically because a sequence of additional authorization keys has already been provided, the method is continued in step 816 using an arbitrary one of these authorization key pairs which are presently available. It should be assumed below that the authorization key pair available for decrypting the data object is the key pair with index i. The authorization key pair with index i comprises a private authorization key Gi received in step 816. A counting index n=i is thereupon set in step 818. Step 820 thereupon involves retrieving a ciphertext, generated previously during activation of the smart card with the new set of authorization keys with index i, from an external database. This ciphertext retrieved in step 820 is the ciphertext which was generated in step 704 in FIG. 7 and was stored in said database in step 706.

Once the ciphertext has been retrieved from the database in step 820, step 822 involves decrypting the ciphertext with the currently available private authorization key with index n, i.e. in the present step index n=i. In other words, the private authorization key of the smart card used for decrypting is used to decrypt the ciphertext. This decryption operation in step 822 yields the private authorization key with index n−1, i.e. index i−1, or in other words the private authorization key of the predecessor smart card in the sequence of smart cards which immediately precedes the smart card with index i.

Step 824 involves checking whether the running index n=1. This is because in this case the private authorization key extracted from the ciphertext in step 822 would correspond to the initial private authorization key G0. If this is the case, after step 824, steps 806 to 814 are carried out, as described above.

It should be assumed below, however, that in step 824 it emerges that n is greater than 1, and so step 824 is followed by step 826 with the running index n being decreased by 1, i.e. n=i−2. After step 826, the method in steps 820 to 824 is repeated, as described above.

This means that in step 820 the ciphertext assigned to the index i−2 is then retrieved from the external database. Using the private authorization key with index i−1 obtained in the previous loop, it is then possible for the ciphertext just retrieved in step 820 in turn to be decrypted, from which the private authorization key with index i−2 is obtained in step 822. That is in turn followed by step 824 with the check to determine whether the running index is 1, i.e. whether the private authorization key obtained in step 822 corresponds to the initial private authorization key G0. If this is the case, step 806 ensues, whereas if this condition is not met, step 826 with the running index n being decreased by 1 is effected.

Consequently, by carrying out steps 820 to 826 recursively with sequential retrieval of corresponding ciphertexts, the initial private authorization key G0 is extracted in order thereby to perform decryption of the encrypted symmetrical key.

LIST OF REFERENCE SYMBOLS

100 Data processing system
102 Input means
104 Screen
106 Interface
108 Processor
110 Memory
112 Applet
114 Module
116 Module
118 Module
120 Network
122 Database
124 User identification
126 Public key
128 Random number
130 Encrypted data object
132 Database
134 Database
150 Ciphertext
152 Smart card
154 Private key
156 Public key
158 Hardware module
160 Smart card
162 Private key
164 Public key
166 Hardware module
200 Applet
202 Module
204 Module
206 Module
208 Data processing system
210 Interface
212 Processor
214 Memory
216 Program
218 Module
220 Module
222 Module

The invention claimed is:

1. A method, comprising the following steps:
receiving an encrypted data object, which is a data object at a computer that has been encrypted using an initial public authorization key of an initial asymmetrical cryptographic key pair that includes an initial private authorization key,
accessing a further private authorization key, which together with a further public authorization key forms a further asymmetrical cryptographic key pair,
retrieving a ciphertext, which comprises the initial private authorization key encrypted with the further public authorization key such that the ciphertext is assigned to the further asymmetrical cryptographic key pair,
decrypting the encrypted initial private authorization key with the further private authorization key,
decrypting the encrypted data object by means of the decrypted initial first private authorization key, and
checking a signature of the encrypted data object, comprising the following steps:
reading a signature of the encrypted data object, and
verifying the signature of the encrypted data object, wherein the verification is effected with the further public authorization key.

2. The method of claim 1, further comprising carrying out instructions on the computer for the step of receiving a key pair identifier assigned to the further asymmetrical cryptographic key pair, wherein the ciphertext is retrieved on the basis of the key pair identifier.

3. The method of claim 1, wherein the ciphertext is retrieved from a database.

4. The method of claim 1, wherein the further asymmetrical key pair is stored together with the ciphertext on a portable data carrier.

5. The method of claim 1, wherein:
the data object is a symmetrical data object key, such that the step of receiving an encrypted data object includes receiving the symmetrical data object key, which has been encrypted with the initial public authorization key, the method further comprises:

receiving a further encrypted data object, which is a further data object that has been encrypted by the symmetrical data object key, performing the step of decrypting the encrypted initial private authorization key with the further private authorization key, decrypting the encrypted symmetrical data object key with the decrypted initial private authorization key, and decrypting the encrypted further data object using the decrypted symmetrical data object key.

6. The method of claim 1, wherein accessing the further private authorization key comprises the following steps:

receiving a user identification and a user identifier assigned to the user identification, retrieving a random value assigned to the user identification from a database, calculating the further private authorization key, wherein the random value and the user identifier are included in the calculation.

7. The method of claim 6, wherein the calculation of the further private authorization key is effected using a function g that is applied to the user identifier, wherein the function g is preferably a one-way function, such as e.g. a cryptographic hash function.

8. The method of claim 6, wherein the user identifier is received as a function value of a function g that was applied to the user identifier, wherein the function g is preferably a one-way function, such as e.g. a cryptographic hash function.

9. The method of claim 6, wherein the further private authorization key is calculated by applying a function f to the random value and g (user identifier).

10. The method of claim 6, wherein the function f is a one-way function, e.g. a cryptographic hash function.

11. The method of claim 6, wherein the signature check furthermore comprises the step of calculating the further public authorization key from the further private authorization key by means of an asymmetrical cryptographic key generating method, wherein the further private and the further public authorization keys form the further asymmetrical cryptographic key pair.

12. The method of claim 6, wherein the random value is retrieved from the database via a secure communication link.

13. The method of claim 6, wherein the random value is stored in encrypted fashion in the database.

14. A non-transitory, computer-readable recording medium containing a computer program comprising executable program instructions for carrying out a method, comprising the following steps:

receiving an encrypted data object, which is a data object that has been encrypted using an initial public authorization key of an initial asymmetrical cryptographic key pair, which includes an initial private authorization key, accessing a further private authorization key, which together with a further public authorization key forms a further asymmetrical cryptographic key pair, retrieving a ciphertext, which comprises the initial private authorization key encrypted with the further public authorization key such that the ciphertext is assigned to the further asymmetrical cryptographic key pair, decrypting the encrypted initial private authorization key with the first further private authorization key, decrypting the encrypted data object by means of the decrypted initial private authorization key, and checking a signature of the encrypted data object, comprising the following steps:

reading a signature of the encrypted data object, and verifying the signature of the encrypted data object, wherein the verification is effected with the further public authorization key.

15. The non-transitory, computer-readable recording medium of claim 14, wherein the method further comprises receiving a key pair identifier assigned to the further asymmetrical cryptographic key pair, wherein the ciphertext is retrieved on the basis of the key pair identifier.

16. The non-transitory, computer-readable recording medium of claim 14, wherein the ciphertext is retrieved from a database.

17. The non-transitory, computer-readable recording medium of claim 14, wherein the further asymmetrical key pair is stored together with the ciphertext on a portable data carrier.

18. The non-transitory, computer-readable recording medium of claim 14, wherein:

the data object is a symmetrical data object key, such that the step of receiving an encrypted data object includes receiving the symmetrical data object key, which has been encrypted with the initial public authorization key, the method further comprises:

receiving a further encrypted data object, which is a further data object that has been encrypted by the symmetrical data object key, performing the step of decrypting the encrypted initial private authorization key with the further private authorization key, decrypting the encrypted symmetrical data object key with the decrypted initial private authorization key, and decrypting the encrypted further data object using the decrypted symmetrical data object key.

19. The non-transitory, computer-readable recording medium of claim 14, wherein accessing the further private authorization key comprises the following steps:

receiving a user identification and a user identifier assigned to the user identification, retrieving a random value assigned to the user identification from a database, calculating the further private authorization key, wherein the random value and the user identifier are included in the calculation.

20. The non-transitory, computer-readable recording medium of claim 19, wherein the calculation of the further private authorization key is effected using a function g that is applied to the user identifier, wherein the function g is preferably a one-way function, such as e.g. a cryptographic hash function.

21. The non-transitory, computer-readable recording medium of claim 19, wherein the user identifier is received as a function value of a function g that was applied to the user identifier, wherein the function g is preferably a one-way function, such as e.g. a cryptographic hash function.

22. The non-transitory, computer-readable recording medium of claim 19, wherein the further private authorization key is calculated by applying a function f to the random value and g (user identifier).

23. The non-transitory, computer-readable recording medium of claim 19, wherein the function f is a one-way function, e.g. a cryptographic hash function.

24. The non-transitory, computer-readable recording medium of claim 19, wherein the signature check furthermore comprises the step of calculating the further public authorization key from the further private authorization key by means of an asymmetrical cryptographic key generating method, wherein the further private and the further public authorization keys form the further asymmetrical cryptographic key pair.

25. The non-transitory, computer-readable recording medium of claim 19, wherein the random value is retrieved from the database via a secure communication link.

26. The non-transitory, computer-readable recording medium of claim 19, wherein the random value is stored in encrypted fashion in the database.

* * * * *

UNITED STATES PATENT AND TRADEMARK OFFICE
Certificate

Patent No. 8,195,951 B2

Patented: June 5, 2012

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Adrian Spalka, Koblenz (DE); and Jan Lehnhardt, Koblenz (DE).

Signed and Sealed this Twelfth Day of March 2013.

FARID HOMAYOUNMEHR
*Supervisory Patent Examiner*
Art Unit 2495
Technology Center 2400